United States Patent
Lievens

(10) Patent No.: US 8,583,248 B2
(45) Date of Patent: Nov. 12, 2013

(54) SYSTEMS, METHODS, AND ARTICLES OF MANUFACTURE FOR CONFIGURING HEARING PROSTHESES

(75) Inventor: Stefan Lievens, Mechelen (BE)

(73) Assignee: Cochlear Limited (AU)

( * ) Notice: Subject to any disclaimer, the term of this patent is extended or adjusted under 35 U.S.C. 154(b) by 0 days.

(21) Appl. No.: 13/176,442

(22) Filed: Jul. 5, 2011

(65) Prior Publication Data

US 2013/0013027 A1    Jan. 10, 2013

(51) Int. Cl.
*A61N 1/36* (2006.01)
(52) U.S. Cl.
USPC .......................................................... 607/57
(58) Field of Classification Search
USPC .................................................... 607/55–57
See application file for complete search history.

(56) References Cited

U.S. PATENT DOCUMENTS

| | | | |
|---|---|---|---|
| 5,626,629 A * | 5/1997 | Faltys et al. | 607/57 |
| 6,289,247 B1 * | 9/2001 | Faltys et al. | 607/57 |
| 7,366,307 B2 | 4/2008 | Yanz et al. | |
| 7,672,468 B2 | 3/2010 | Kaiser et al. | |
| 8,170,679 B2 * | 5/2012 | Saoji et al. | 607/57 |
| 8,209,026 B1 * | 6/2012 | Saoji et al. | 607/57 |
| 2005/0187592 A1 * | 8/2005 | Seligman et al. | 607/57 |
| 2011/0060385 A1 | 3/2011 | Lineaweaver | |

FOREIGN PATENT DOCUMENTS

WO    2004017880 A1    3/2004

OTHER PUBLICATIONS

International Search Report for Internation Patent Application No. PCT/IB2012/053424 mailed Feb. 27, 2013 (13 pages).

* cited by examiner

*Primary Examiner* — George Evanisko
(74) *Attorney, Agent, or Firm* — McDonnell Boehnen Hulbert & Berghoff LLP

(57) ABSTRACT

The present application discloses systems, methods, and articles of manufacture for fitting a hearing prosthesis to a hearing prosthesis recipient. Some embodiments include generating a first set of two or more stimulation signals via a corresponding set of two or more channels of a hearing prosthesis, reducing the corresponding stimulation levels of the stimulation signals of the first set of two or more stimulation signals in response to receiving an indication that a sound sensation corresponding to the first set of two or more stimulation signals is uncomfortably loud, and generating a second set of one or more stimulation signals at the reduced stimulation levels via a first subset of one or more channels.

10 Claims, 11 Drawing Sheets

SYSTEMS, METHODS, AND ARTICLES OF MANUFACTURE FOR CONFIGURING HEARING PROSTHESES

BACKGROUND

Various types of hearing prostheses provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural stimulation signals, or any other part of the ear, auditory nerve, or brain that may process the neural stimulation signals.

Persons with some forms of conductive hearing loss may benefit from hearing prostheses, such as acoustic hearing aids or vibration-based hearing aids. An acoustic hearing aid typically includes a small microphone to detect sound, an amplifier to amplify certain portions of the detected sound, and a small speaker to transmit the amplified sounds into the person's ear. Vibration-based hearing aids typically include a small microphone to detect sound, and a vibration mechanism to apply vibrations corresponding to the detected sound to a person's bone, thereby causing vibrations in the person's inner ear, thus bypassing the person's auditory canal and middle ear. Types of vibration-based hearing aids include bone anchored hearing aids, direct acoustic cochlear stimulation devices, or other vibration-based devices. A bone anchored hearing aid typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing aids may use similar vibration mechanisms to transmit sound via direct vibration of teeth or other cranial or facial bones.

Persons with certain forms of sensorineural hearing loss may benefit from cochlear implants and/or auditory brainstem implants. For example, cochlear implants can provide a person having sensorineural hearing loss with the ability to perceive sound by stimulating the person's auditory nerve via an array of electrodes implanted in the person's cochlea. An external component of the cochlear implant detects sound waves, which are converted into a series of electrical stimulation signals delivered to the implant recipient's cochlea via the array of electrodes. Auditory brainstem implants use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem can help persons with sensorineural hearing loss to perceive sound.

The effectiveness of any of the above-described prostheses depend not only on the design of the prosthesis itself but also on how well the prosthesis is configured for or "fitted" to a prosthesis recipient. The fitting of the prosthesis, sometimes also referred to as "programming" or "mapping," creates a set of configuration settings and other data that defines the specific characteristics of the stimulation signals (acoustic, mechanical, or electrical) delivered to the relevant portions of the person's outer ear, middle ear, inner ear, auditory nerve, brain stem, etc. This configuration information is sometimes referred to as the recipient's "program" or "MAP."

Hearing prostheses are usually fitted to a prosthesis recipient by an audiologist or other similarly trained professional who may use a sophisticated fitting program to individually set multiple stimulation signal levels for multiple channels of the hearing prosthesis. Although sophisticated fitting programs may give an audiologist or other similarly trained professional a great deal of control and flexibility over the hearing prosthesis fitting parameters, fitting a prosthesis to a recipient with these sophisticated fitting programs can be complicated and time consuming even for trained professionals.

SUMMARY

The present application discloses systems, methods, and articles of manufacture for configuring a hearing prosthesis for use by a hearing prosthesis recipient.

Some embodiments include generating a first set of two or more stimulation signals via a corresponding set of two or more channels of the hearing prosthesis. Individual stimulation signals have corresponding stimulation levels. In some embodiments, the first set of two or more stimulation signals correspond to a sound having a substantially flat frequency spectrum over a first frequency band.

In response to receiving an indication that a sound sensation corresponding to the first set of two or more stimulation signals is not uncomfortably loud, some embodiments include increasing the corresponding stimulation levels of the individual stimulation signals of the first set of two or more stimulation signals and generating the first set of two or more stimulation signals at the increased stimulation levels via the corresponding set of two or more channels.

In response to receiving an indication that a sound sensation corresponding to the first set of two or more stimulation signals is uncomfortably loud, some embodiments include reducing the corresponding stimulation levels of the stimulation signals of the first set of two or more stimulation signals and generating a second set of one or more stimulation signals at the reduced stimulation levels via a first subset of one or more channels. In some embodiments, the set of two or more channels includes every channel in the first subset of one or more channels. And similar to the first set of two or more stimulation signals, the second set of one or more stimulation signals corresponds to a sound with a substantially flat frequency spectrum over a second frequency band.

Some embodiments also include dividing the set of two or more channels into at least the first subset of one or more channels and a second subset of one or more channels. In some embodiments, dividing the set of two or more channels into at least the first subset of one or more channels and the second subset of one or more channels is part of an initialization procedure performed prior to the steps of (i) generating the first set of two or more stimulation signals via the corresponding set of two or more channels, (ii) reducing the corresponding stimulation levels of the stimulation signals of the first set of two or more stimulation signals, and (iii) generating the second set of one or more stimulation signals at the reduced stimulation levels via the first subset of one or more channels. In other embodiments, dividing the set of two or more channels into at least the first subset of one or more channels and the second subset of one or more channels is performed in response to receiving the indication that the sound sensation corresponding to the first set of two or more stimulation signals is uncomfortably loud.

Some embodiments also include determining at least one of a stimulation level, a pulse width, and a phase gap for individual stimulation signals of the first set of two or more stimulation signals prior to generating the first set of two or more stimulation signals via the corresponding set of two or more channels of the hearing prosthesis. Embodiments also include determining at least one of a pulse width and a phase gap for individual signals of the second set of one or more stimulation signals prior to instructing the hearing prosthesis to generate the second set of one or more stimulation signals at the reduced stimulation levels via the first subset of one or more channels.

For example, in some embodiments, at least one of a corresponding stimulation level, pulse width, pulse rate, or phase gap of one or more individual stimulation signals of the first set of two or more stimulation signals are increased in response to receiving an indication that a sound sensation corresponding to the first set of two or more stimulation signals is not uncomfortably loud. Similarly, at least one of a corresponding stimulation level, pulse width, pulse rate, or phase gap of one or more individual stimulation signals of the first set of two or more stimulation signals is reduced in response to receiving an indication that the sound sensation corresponding to the first set of two or more stimulation signals is uncomfortably loud.

As described above, some embodiments also include reducing the corresponding stimulation levels of the stimulation signals of the first set of two or more stimulation signals and instructing the hearing prosthesis to generate a second set of one or more stimulation signals at the reduced stimulation levels via a first subset of one or more channels. Some embodiments further include reducing the corresponding stimulation levels of the stimulation signals of the second set of one or more stimulation signals in response to receiving an indication that a sound sensation corresponding to the second set of one or more stimulation signals is uncomfortably loud, and instructing the hearing prosthesis to generate a third set of one or more stimulation signals at the reduced stimulation levels via a second subset of one or more channels. In some embodiments, the first subset of one or more channels includes all of the channels in the second subset of one or more channels. In other embodiments, the second subset of one or more channels is mutually exclusive of the first subset of one of more channels.

In some embodiments, certain aspects of some of the disclosed features and functions are performed by the hearing prosthesis. In some other embodiments, certain aspects of some of the disclosed features and functions are performed by a computing device associated with the hearing prosthesis. In still further embodiments, one or more features and functions are performed by the hearing prosthesis while other features and functions are performed by a computing device associated with the hearing prosthesis.

BRIEF DESCRIPTION OF THE DRAWINGS

FIGS. 3A-4F show some examples of configuring a hearing prosthesis according to some embodiments of the disclosed systems, methods, and articles of manufacture.

FIG. 4 shows an example of different groupings of hearing prosthesis channels according to some embodiments of the disclosed systems, methods, and articles of manufacture.

DETAILED DESCRIPTION

The following detailed description describes various features, functions, and attributes of the disclosed systems, methods, and articles of manufacture with reference to the accompanying figures. In the figures, similar symbols typically identify similar components, unless context dictates otherwise. The example embodiments described herein are not meant to be limiting. Certain aspects of the disclosed systems, methods, and articles of manufacture can be arranged and combined in a wide variety of different configurations, all of which are contemplated herein. For illustration purposes, some features and functions are described with respect to cochlear implants. However, many of the disclosed features and functions may be equally applicable to other types of multi-channel hearing prostheses now known or later developed, which may include, for example, acoustic hearing aids, bone anchored hearing aids, direct acoustic cochlear stimulation devices, vibration-based mechanisms to transmit sound via direct vibration of teeth or other cranial or facial bones, auditory brainstem implants, hybrid hearing devices, or other types hearing prostheses.

Hearing Prostheses

Figure 1:
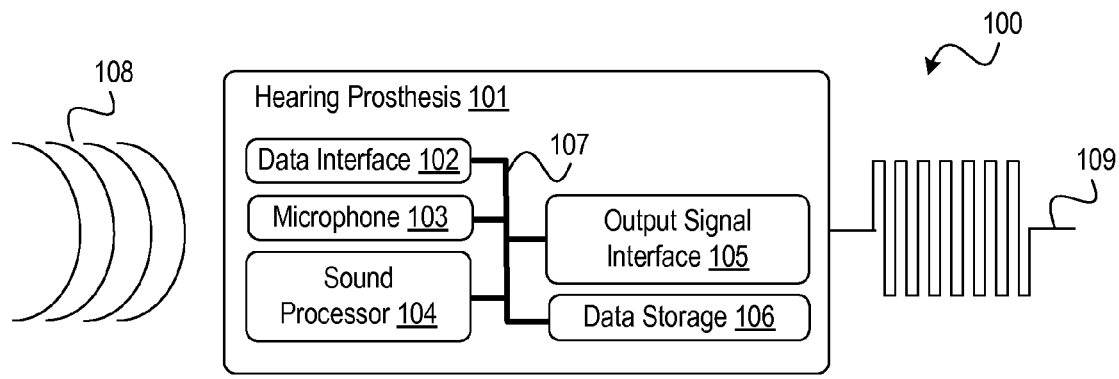
FIG. 1 shows one example of a hearing prosthesis configured according to some embodiments of the disclosed systems, methods, and articles of manufacture.

FIG. 1 shows one example 100 of a hearing prosthesis 101 configured according to some embodiments of the disclosed systems, methods, and articles of manufacture. The hearing prosthesis 101 may be a cochlear implant, an acoustic hearing aid, a bone anchored hearing aid or other vibration-based hearing prosthesis, a direct acoustic stimulation device, an auditory brain stem implant, or any other type of multi-channel hearing prosthesis configured to aid a prosthesis recipient in hearing sound.

The hearing prosthesis 101 includes a data interface 102, a microphone 103, a sound processor 104, an output signal interface 105, and data storage 106, all of which are connected directly or indirectly via circuitry 107. In other embodiments, the hearing prosthesis 101 may have additional or fewer components than the prosthesis shown in FIG. 1. Additionally, the components may be arranged differently than shown in FIG. 1. For example, depending on the type and design of the hearing prosthesis, the illustrated components may be enclosed within a single operational unit or distributed across multiple operational units (e.g., an external unit, an internal unit, etc.). Similarly, in some embodiments, the hearing prosthesis 101 may additionally include one or more processors (not shown) configured to determine configuration settings for its sound processor 104.

In embodiments where the hearing prosthesis 101 is a cochlear implant, the microphone 103 receives acoustic signals 108, and the sound processor 104 analyzes and encodes the acoustic signals 108 into a group of electrical stimulation signals 109 for application to an implant recipient's cochlea via an output signal interface 105 communicatively connected to an array of electrodes.

Stimulation Signals

Figure 2:
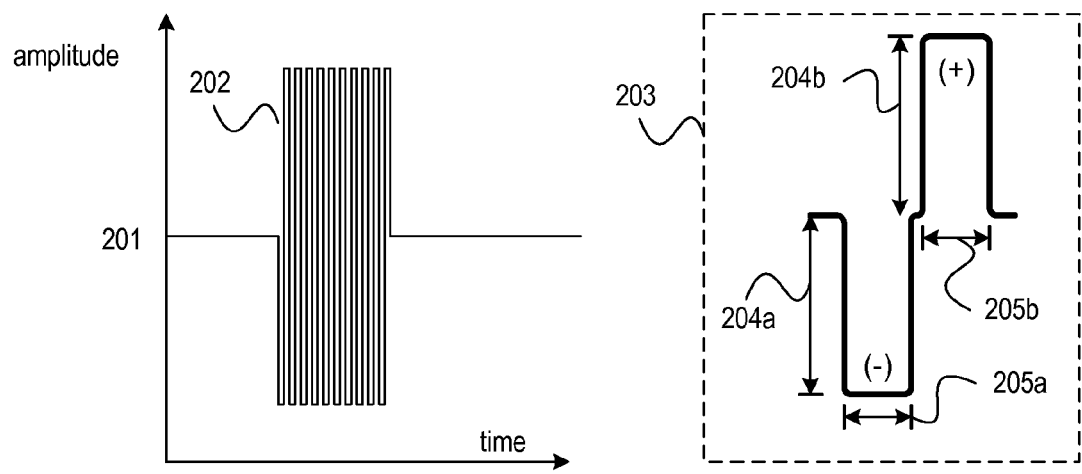
FIG. 2 shows an example of an electrical stimulation signal for embodiments where the hearing prosthesis is a cochlear implant.

FIG. 2 shows an example of an electrical stimulation signal 202 for embodiments where the hearing prosthesis 101 is a cochlear implant. The stimulation signal 202 is one signal of the group of stimulation signals 109 shown in FIG. 1.

The stimulation signal 202 shown in FIG. 2 is generated and applied to a prosthesis recipient via one channel 201 of a cochlear implant. A typical cochlear implant has multiple channels. The stimulation signal 202 includes a group of substantially square wave pulses, but other types of waveforms could be used as well, such as, for example, sinusoidal or triangular waves or wave pulses.

An expanded view of one current pulse 203 of the stimulation signal 202 is shown in the inset. The current pulse 203 of the stimulation signal 202 shown here is a charge-balanced, biphasic current pulse having an amplitude and pulse width. In some embodiments, the biphasic current pulse may also have a phase gap (not shown) between the positive and negative phases of the pulse. The absolute values of the amplitude 204a and pulse width 205a of the negative phase of the current pulse 203 are substantially the same as the absolute values of the amplitude 204b and pulse width 205b of the positive phase of the current pulse 203. As a result, the electrical stimulus delivered to a nerve in the positive phase of the current pulse 203 is substantially the same as the electrical stimulus delivered to the nerve in the negative phase of the current pulse 203 so that substantially no net charge remains after the completion of an individual current pulse. The stimulation signal 202 includes multiple biphasic current pulses similar to the biphasic current pulse 203.

In the biphasic current pulse 203 shown in FIG. 2, the amplitude 204 corresponds to a level of electrical current delivered via the stimulation channel 201. The pulse width 205 corresponds to the amount of time that the current is applied via the stimulation channel 201, and is expressed in microseconds (μs) per phase of the biphasic current pulse 203.

A charge per phase of the biphasic current pulse 203 is calculated by multiplying the amplitude 204 of the biphasic current pulse 203 by the pulse width 205 of the biphasic current pulse 203. A biphasic current pulse with a higher charge per phase causes the recipient to experience a louder sound sensation than a biphasic pulse with a lower charge per phase. Because the charge per phase is the product of the amplitude and pulse width, increasing one or both of the amplitude and/or the pulse width of a biphasic current pulse causes the recipient to experience a louder sound sensation, and decreasing one or both of the amplitude and/or the pulse width of the biphasic current pulse causes the recipient to experience a softer sound sensation.

Configuring Hearing Prostheses

FIGS. 3A-3F show examples of configuring hearing prostheses according to some embodiments of the disclosed systems, methods, and articles of manufacture. The examples shown in FIGS. 3A-3F are described with respect to cochlear implants and user interfaces for cochlear implants. However, the features and functions shown and described with respect to the disclosed embodiments can be used with other types of hearing prostheses and their corresponding user interfaces.

Figure 3A:
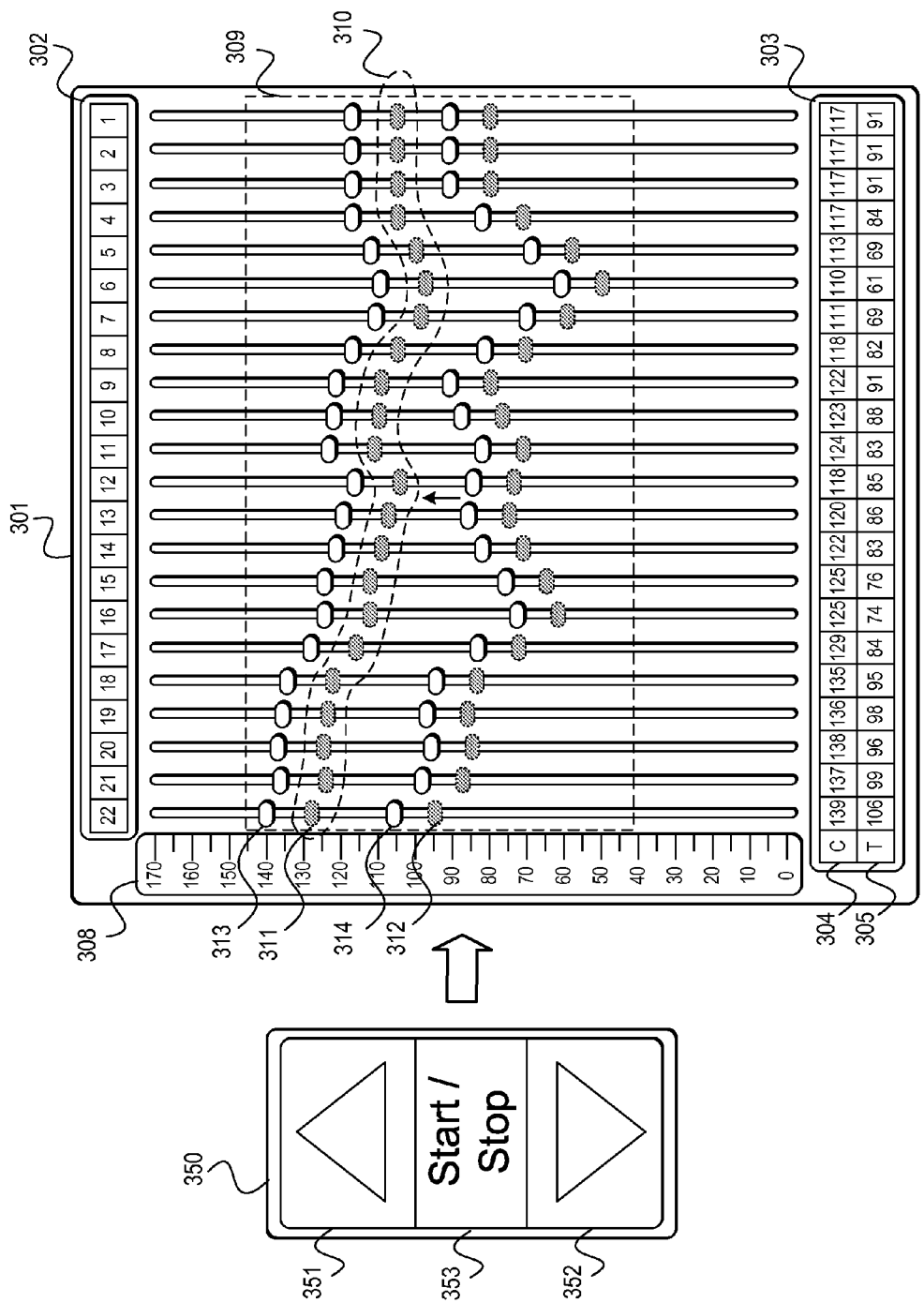

FIG. 3A shows an example complex user interface 301 and an example simplified user interface 350 for configuring a cochlear implant. The user interfaces 301, 350 are implemented as software running on computing devices. In some embodiments, the simplified user interface 350 is implemented on a different type of computing device than the complex user interface 301. For example, the simplified user interface 350 may be implemented on a smaller hand-held computing device whereas the complex user interface 301 may be implemented on a larger computing device, such as a tablet computer, desktop computer, laptop computer, etc. In some embodiments, the simplified user interface 350 may be implemented with physical buttons on a remote-control type of device. In other embodiments, the simplified user interface 350 may be implemented on a smart-phone or other type of hand-held computing device with a touch-screen interface.

Configuring a cochlear implant for a particular recipient includes configuring the individual channel settings for the channels of the cochlear implant. For a cochlear implant, an individual channel may include at least one active electrode and at least one reference electrode of an array of cochlear implant electrodes. The at least one active electrode of an individual channel is the current source for the stimulation signals to be applied via that channel, and the at least one reference electrode of the channel is the current sink for the stimulation signals to be applied via that channel. The configuration settings for a particular channel define the attributes of the stimulation signals that are generated via that particular channel.

The complex user interface 301 shown in FIG. 3A is designed for use with a cochlear implant equipped with 22 channels. Similar user interfaces may be used with other cochlear implants having greater than or less than 22 stimulation channels. Likewise, user interfaces for use with other types of hearing prostheses may have greater than or less than 22 channel controllers.

The complex user interface 301 has an individual channel controller for each individual channel of the cochlear implant. Each channel controller is used to configure the attributes of the stimulation signals that are generated by the individual channel corresponding to the individual channel controller. Typically, a cochlear implant has two stimulation levels to configure for each channel: (1) the Threshold Level, or "T-level"; and (2) the Comfort Level, or "C-level." T-levels and C-levels may vary from recipient to recipient and from channel to channel. Other configuration parameters may also be set for a particular channel, such as a stimulation signal pulse rate, a stimulation signal pulse width, a phase gap, or other signal attributes, such as the stimulation signal attributes shown and described with respect to FIG. 2.

For a cochlear implant, the T-level setting for a particular channel corresponds to the lowest level of current for a stimulation signal generated via that channel that causes the recipient to experience a sound sensation. In contrast, the C-level corresponds to the maximum level of current for a stimulation signal that still feels comfortable to the recipient. The T-levels and the C-levels determine in part how well the implant recipient hears and understands detected speech and/or sound, but the C-levels tend to affect how speech sounds to the recipient more than the T-levels because most of the acoustic speech signal is generally mapped onto approximately the top 20% of the range between the T-level and C-level.

Although the terminology and abbreviations may be device-specific, the general purpose of setting individual threshold and comfort levels for individuals channels is to determine a recipient's dynamic range for each channel by defining a lowest intensity level (T-level) and a highest acceptable intensity level (C-level) for the stimulation signals for each channel. Other hearing prostheses may have similar maximum and minimum intensity levels, such as, for example, maximum and minimum acoustic levels or maximum and minimum mechanical vibration levels.

As previously described, the complex user interface 301 shown in FIG. 3A is designed for use with a cochlear implant equipped with 22 channels. Box 302 across the top of the complex user interface 301 shows a channel number for each of the 22 channels of the cochlear implant. Box 303 across the bottom of the complex user interface 301 shows a set of C-levels 304 and a set of T-levels 305. The set of C-levels 304 includes a C-level setting for each of the 22 channels of the cochlear implant, and the set of T-levels 305 includes a T-level setting for each of the 22 channels of the cochlear implant.

In the complex user interface 301, the C-level and T-level for a particular channel are also shown on a channel slider bar corresponding to that particular channel. For example, the C-level for channel 22 is set to a value of 139 and is indicated on the slider bar associated with channel 22 by slider 313. Similarly, the T-level for channel 22 is set to a value of 106 and is indicated on the slider bar associated with channel 22 by slider 314. The position of sliders 313 and 314 correspond to the numeric values shown on the axis 308 along the left side of the complex user interface 301. In this manner, the numeric values of the C-level and T-level for each channel shown in box 303 along the bottom of the complex user interface 301 correspond to the positions of the sliders on each corresponding channel bar. The C-level and T-level settings shown in the complex user interface 301 correspond to the configured C-level and T-level settings for the cochlear implant.

Because the complex user interface 301 enables each C-level and each T-level for each of the 22 channels to be individually adjusted, the complex user interface 301 provides a very high degree of flexibility in the fitting process for a finely-tuned fitting of the cochlear implant to a particular recipient. However, typically only an audiologist or other similarly-trained professional can use the complex user interface 301 to configure a hearing prosthesis for a particular recipient because of the complexity of the controls. Additionally, implementing the complex user interface 301 on a small hand-held computing device is impractical because the screen is too small to display all the controls at an acceptable size. A user interface with fewer controls would be easier to implement on a small hand-held computing device and make the fitting procedure accessible to an untrained professional or even the prosthesis recipient.

FIG. 3A shows such a simplified user interface 350 that can be used instead of (or in addition to) the complex user interface 301. The simplified user interface 350 includes an "up" input 351 and a "down" input 352. In operation, the up input 351 is used to increase the stimulation levels of the 22 channels of the cochlear implant, and the down input 352 is used to decrease the stimulation levels of the 22 channels of the cochlear implant.

For example, in FIG. 3A, a user (e.g., the implant recipient or an audiologist) increases the stimulation levels (i.e., just the C-levels, just the T-levels, or both the C-levels and T-levels) in the set of channels 309 by activating the up input 351 of the simplified user interface 350. In particular, the top row of shaded indicators 310 corresponds to previous C-level settings for the set of channels 309, and the top row of unshaded indicators corresponds to C-level settings after one or more inputs from the up input 351 of the simplified user interface 350. For example, with reference to channel 22, the shaded slider 311 corresponds to a previous C-level setting for channel 22 having a value of 129, and the shaded slider 312 corresponds to a previous T-level setting for channel 22 having a value of 96. Similarly, the slider 313 corresponds to the C-level setting for channel 22 having a value of 139 after one or more inputs via the up input 351 of the simplified user interface 350, and the slider 314 corresponds to the T-level setting for channel 22 having a value of 106 after one or more inputs via the up input 351 of the simplified user interface 350.

Because the simplified user interface 350 has a very small set of controls compared to the complex user interface 301, some users (including hearing prosthesis recipients and/or audiologists) may find the simplified user interface 350 much easier to use than the complex user interface 301. Additionally, with only a few controls, the simplified user interface 350 is practical for implementing on a small hand-held computing device, e.g., a smart phone or other small computing platform, which makes the simplified user interface 350 more convenient to use than the complex user interface 301, which typically requires a much larger computer screen to display all the controls.

However, one potential drawback of using the most basic aspects of the simplified user interface 350 shown and described in FIG. 3A is that, when increasing or decreasing the stimulation levels of all of the channels 309 at the same time, a recipient may stop increasing the stimulation levels when the stimulation level of a stimulation signal on just one of the channels begins to cause discomfort. As a result, the stimulation levels of other channels may not be set to their highest potential setting. And if the stimulation levels of the other channels are not set to their highest potential setting, the recipient may not hear as well as he or she might otherwise be able to hear with a better configured prosthesis.

To ameliorate or otherwise minimize the above-described potential shortcoming of using the most basic aspects of the simplified user interface 350 shown and described in FIG. 3A during the prosthesis fitting process, some embodiments of the disclosed systems, methods, and articles of manufacture may include additional advanced features and functions described herein.

For example, in some embodiments, during the fitting process, the simplified user interface 350 causes the hearing prosthesis to generate a first set of stimulation signals via a corresponding set of channels of the hearing prosthesis, such as the set of channels 309 that includes all 22 channels. With reference to FIG. 3A, activating the "Start/Stop" input 353 (or a similar input) of the simplified user interface 350 causes the prosthesis, alone or in combination with the simplified user interface 350, to initiate a fitting algorithm. The fitting algorithm includes generating (or causing the prosthesis to generate) a first set of stimulation signals via the set of channels 309. In some embodiments, the first set of stimulation signals corresponds to a sound having a substantially flat frequency spectrum over a frequency band corresponding to the frequency range of the set of channels 309. In some embodiments, the sound corresponds to white noise. In other embodiments, however, the sound need not be white noise nor even have a substantially flat frequency spectrum.

When the prosthesis generates the first set of stimulation signals via the set of channels 309, the prosthesis recipient experiences a sound sensation corresponding to the first set of stimulation signals. In response, the prosthesis recipient can indicate whether the sound sensation corresponding to the first set of stimulation signals is (or is not) uncomfortably loud via the up input 351 or the down input 352 of the simplified user interface 350. For example, if the sound sensation is not uncomfortably loud, then the prosthesis recipient may press the up input 351 to increase the stimulation levels, but if the sound sensation is uncomfortably loud, then the prosthesis recipient may press the down input 352 to decrease the stimulation levels.

In some embodiments, in response to receiving an indication that the sound sensation corresponding to the first set of stimulation signals generated via the set of channels 309 is not uncomfortably loud, the hearing prosthesis (i) increases the stimulation levels of the first set of stimulation signals and (ii) generates the first set of stimulation signals again via the set of channels 309, but at the increased stimulation levels.

For example, in FIG. 3A, the shaded sliders show the initial positions of the T-levels and C-levels, and the non-shaded sliders show the positions of the T-levels and C-levels after having been increased by 10 units from the initial positions. In operation, the C-levels and T-levels may be increased by 1 unit (as shown on the axis 308 on the left side of the complex user interface 401) in response to an individual indication that the sound sensation corresponding to the stimulation signals generated via the set of channels 309 is not uncomfortably loud. However, in other embodiments, the C-levels and T-levels may be increased by more than 1 unit in response to an individual indication that the corresponding sound sensation is not uncomfortably loud. Similarly, in some embodiments, the C-levels may be increased while the T-levels may remain unchanged. Additionally, in some embodiments, the stimulation levels may be increased by a percentage amount (e.g., 1%) instead of a fixed unit or number of units.

The example shown in FIG. 3A shows one embodiment where the stimulation levels of the first set of stimulation signals are increased in response to receiving an indication that the sound sensation corresponding to the first set of stimulation signals generated via the set of channels 309 is not uncomfortably loud. However, some embodiments may additionally or alternatively include increasing one or more of the stimulation signal pulse rates, the stimulation signal pulse widths, and/or the stimulation signal phase gaps of the stimulation signals in the first set of stimulation signals in response to receiving the indication that the sound sensation corresponding to the first set of stimulation signals generated via the set of channels 309 is not uncomfortably loud. At least for cochlear implants, the charge per phase of a particular stimulation signal is the product of the stimulation signal amplitude (determined by the C-levels and T-levels) and the stimulation signal pulse width. As a result, increasing one or both of the amplitude (by increasing the C-levels) and/or the pulse width of the stimulation signal on a particular channel of a cochlear implant increases the sound sensation corresponding to the stimulation signal on that particular channel (i.e., increase the volume).

In response to receiving an indication that the sound sensation corresponding to the first set of stimulation signals generated via the set of channels 309 is uncomfortably loud, the hearing prosthesis (i) reduces the stimulation levels of the first set of stimulation signals (FIG. 3B) and (ii) generates a second set of stimulation signals at the reduced stimulation levels via a first subset 319 (FIG. 3C) of the original set of channels 309.

Figure 3B:
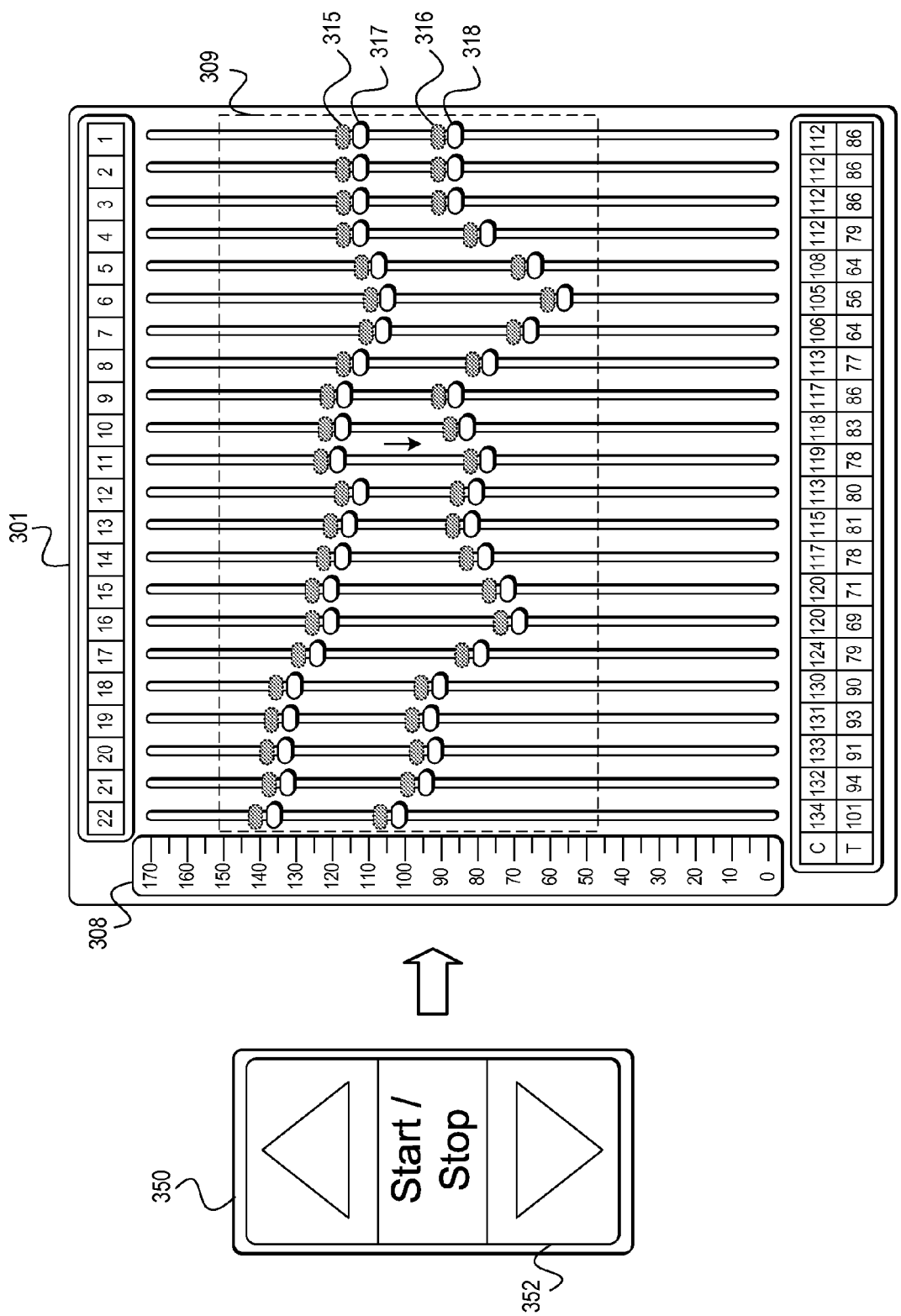

FIG. 3B shows the stimulation levels (e.g., the C-levels and T-levels) of the first set of stimulation signals generated via the set of channels 309 being reduced in response to receiving an indication that the sound sensation corresponding to the first set of stimulation signals generated via the original set of channels 309 is uncomfortably loud. The indication that the sound sensation corresponding to the first set of stimulation signals is uncomfortably loud is an input from the prosthesis recipient via the down input 352 of the simplified user interface 350. However, the indication may be received through other types of inputs on other types of user interfaces as well.

In FIG. 3B, the stimulation levels of the first set of stimulation signals associated with the set of channels 309 have been uniformly reduced by 5 units, as shown on the axis 308 on the left side of the complex user interface 301. For example, with reference to channel 1, the shaded slider 315 corresponds to the previous C-level setting for channel 1 having a value of 117 (see FIG. 3A), and the shaded slider 316 corresponds to the previous T-level setting for channel 1 having a value of 91 (see FIG. 3A). The slider 317 corresponds to the C-level setting for channel 1 having a value of 112, and the slider 318 corresponds to the T-level setting for channel 1 having a value of 86 after the stimulation levels of the first set of stimulation signals have been reduced by 5 units in response to receiving the indication that the sound sensation corresponding to the first set of stimulation signals is uncomfortably loud. Channels 2-22 in the set of channels 309 have similarly been reduced by 5 units.

Although the example of FIG. 3B shows the stimulation levels for the stimulation signals on all 22 channels in the set of channels 309 having been reduced by 5 units, other embodiments may reduce the stimulation levels by more or less than 5 units. Similarly, the example of FIG. 3B shows both the C-levels and T-levels being reduced by 5 units, but some embodiments may reduce only the C-levels while leaving the T-levels constant. Additionally, the example of 3B shows all the stimulation levels being reduced by a uniform number of units, but in some embodiments, the stimulation levels may be reduced by percentages rather than units. For example, instead of reducing all the stimulation levels by 5 units, as measured by the index 308, all of the stimulation levels could be reduced by 5% or 1% or any other percentage amount.

The example shown in FIG. 3B shows one embodiment where the stimulation levels of the first set of stimulation signals are reduced in response to receiving an indication that the sound sensation corresponding to the first set of stimulation signals generated via the set of channels 309 is uncomfortably loud. However, some embodiments may additionally or alternatively include increasing one or more of the stimulation signal pulse rates, the stimulation signal pulse widths, and/or the stimulation signal phase gaps of the stimulation signals in the first set of stimulation signals in response to receiving the indication that the sound sensation corresponding to the first set of stimulation signals generated via the set of channels 309 is uncomfortably loud. At least for cochlear implants, the charge per phase of a particular stimulation signal is the product of the stimulation signal amplitude (determined by the C-levels and T-levels) and the stimulation signal pulse width. As a result, reducing one or both of the amplitude (by reducing the C-levels) and/or the pulse width of the stimulation signal on a particular channel of a cochlear implant may reduce the sound sensation corresponding to the stimulation signal on that particular channel (i.e., decrease the volume).

Figure 3C:
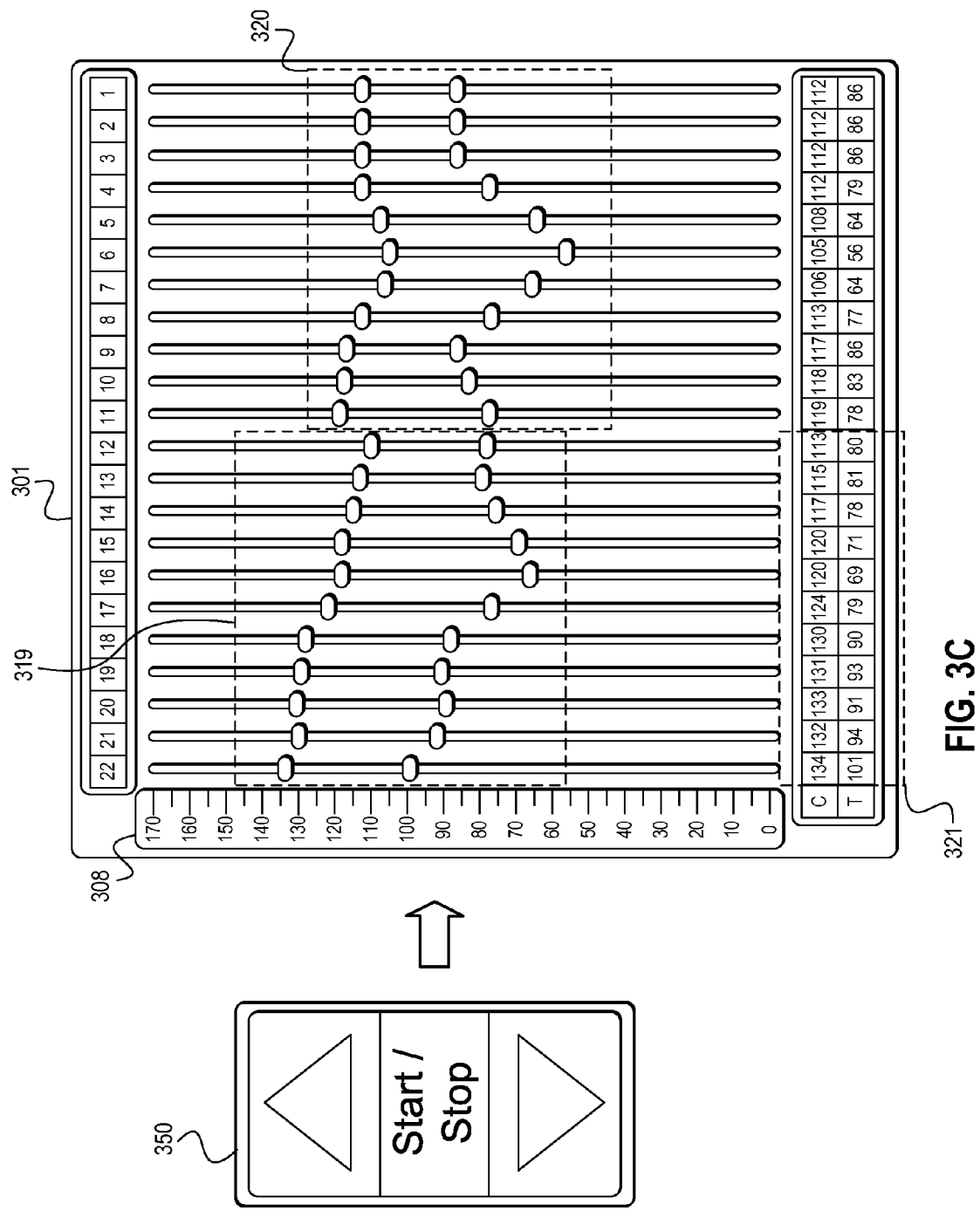

The example shown in FIG. 3B illustrates the first of at least two actions that are performed in response to receiving an indication that the sound sensation corresponding to the first set of stimulation signals is uncomfortably loud. In particular, FIG. 3B shows one example of reducing the stimulation levels of the first set of stimulation signals in response to receiving an indication that a sound sensation corresponding to the first set of stimulation signals is uncomfortably loud. FIG. 3C shows the second of at least two actions taken in response to receiving the indication that the sound sensation corresponding to the first set of stimulation signals is uncomfortably loud. In particular, FIG. 3C shows one example of generating a second set of stimulation signals at the reduced stimulation levels via a first subset 319 of the original set of channels 309 (FIGS. 3A-B).

FIG. 3C shows the set of channels 309 (FIGS. 3A-B) divided into (i) a first subset 319 of one or more channels including channels 12-22 and (ii) a second subset 320 of one or more channels including channels 1-11. Although the first subset 319 and second subset 320 shown in FIG. 3C include equal numbers of channels, the first and second subsets in some embodiments may include unequal numbers of channels. Similarly, in some embodiments, the original set 309 of channels (FIGS. 3A-B) are divided into more than two subsets, e.g., three, four, or more subsets.

Some embodiments include dividing the original set of channels 309 (FIGS. 3A-B) into the first subset 319 of one or more channels and the second subset 320 of one or more channels in response to receiving the indication that the sound sensation corresponding to the first set of stimulation signals generated via the original set of channels 309 (FIGS. 3A-B) is uncomfortably loud. Other embodiments include dividing the original set of channels 309 (FIGS. 3A-B) into the first subset 319 of one or more channels and the second subset 320 of one or more channels as part of an initialization procedure. In some embodiments, the initialization procedure divides and assigns some or all 22 channels to various sets and subsets (or other groupings and/or subgroupings) before the first set of stimulation signals are generated via the corresponding original set of channels 309 (FIGS. 3A-B). Dividing the channels into various sets and subsets as part of an initialization procedure is described in more detail herein with respect to FIG. 4.

Regardless of when (or how) the original set of channels 309 (FIGS. 3A-B) may have been divided into the first subset 319 of one or more channels and the second subset 320 of one of more channels, the aforementioned second of at least two actions that are taken in response to receiving the indication that the sound sensation corresponding to the first set of stimulation signals is uncomfortably loud is the act of generating a second set of stimulation signals at the reduced stimulation levels via a first subset 319 of the original set of channels 309 (FIGS. 3A-B).

In FIG. 3C, a second set of stimulation signals is generated at the reduced stimulation levels via the first subset 319 of one or more channels. For example, the reduced stimulation levels for each of the 11 channels (channels 12-22) in the first subset 319 of one or more channels are shown in box 321 at the bottom of the complex user interface 301. In some embodiments, the second set of stimulation signals corresponds to a sound have a substantially flat frequency spectrum over a particular frequency band. In some embodiments, the particular frequency band corresponds to the frequencies assigned to the channels in the first subset 319 of one or more channels. For example, in FIG. 3C, if particular audio frequency ranges have been assigned to particular channels of the prosthesis, the second set of one or more stimulation signals is based on a sound having a substantially flat frequency spectrum across the frequencies corresponding to the channels in the first subset 319 of one or more channels. In some embodiments, the sound corresponds to white noise. In other embodiments, however, the sound need not be white noise nor even have a substantially flat frequency spectrum.

Figure 3D:
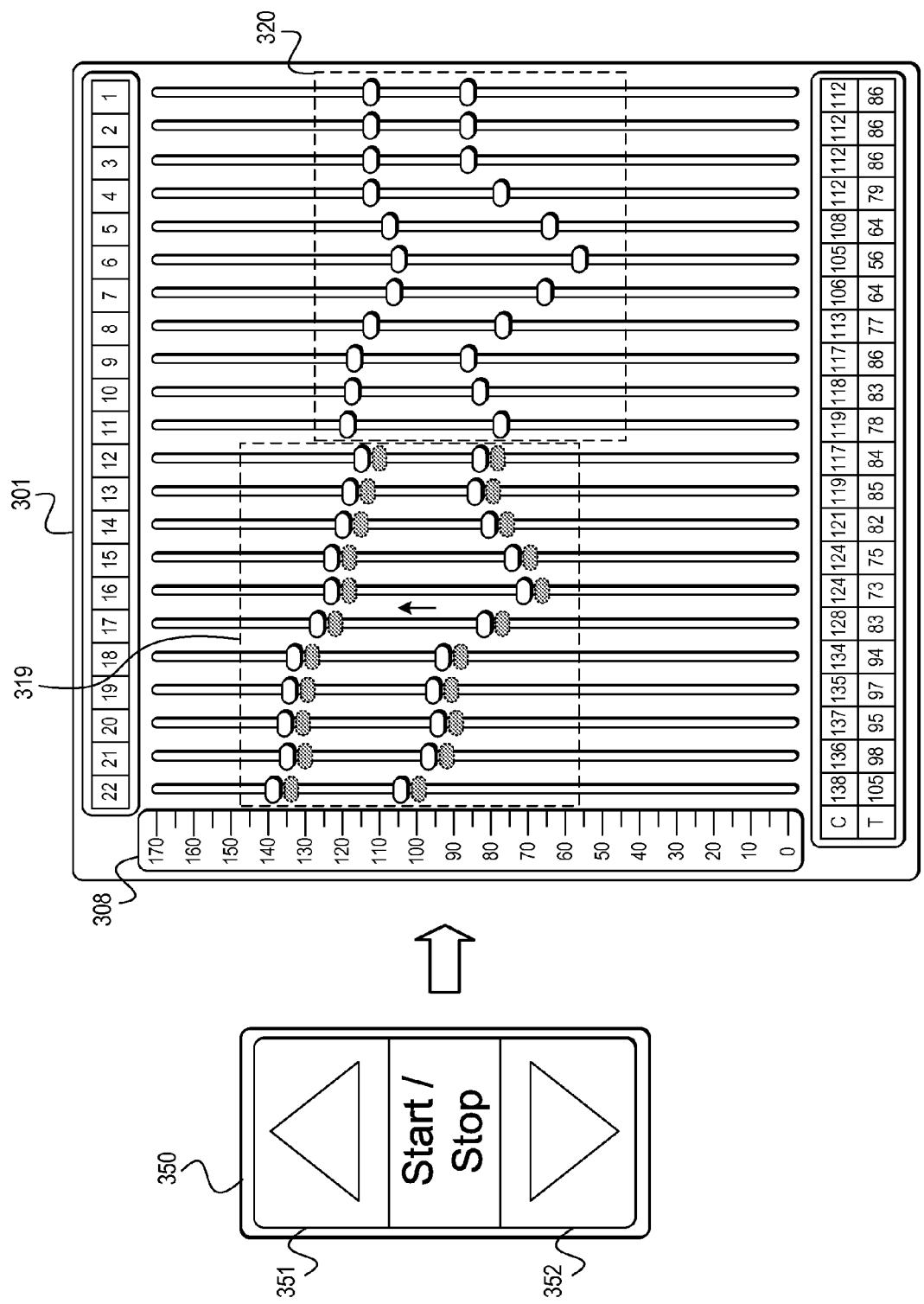

In FIG. 3D, the fitting procedures continue with the first subset 319 of one or more channels. In particular, the second set of stimulation signals is generated via the first subset 319 of one or more channels. When the prosthesis generates the second set of stimulation signals via the first subset 319 of channels, the prosthesis recipient experiences a sound sensation corresponding to the second set of stimulation signals. In response, the prosthesis recipient indicates whether the sound sensation corresponding to the second set of stimulation signals is (or is not) uncomfortably loud via the up input 351 or the down input 352 of the simplified user interface 350. For example, if the sound sensation is not uncomfortably loud, then the prosthesis recipient may press the up input 351 to increase the stimulation levels, but if the sound sensation is uncomfortably loud, then the prosthesis recipient may press the down input 352 to decrease the stimulation levels.

In response to receiving an indication that the sound sensation corresponding to the second set of stimulation signals generated via the first subset 319 of channels is not uncomfortably loud, the hearing prosthesis (i) increases the stimulation levels of the second set of stimulation signals and (ii) generates the second set of stimulation signals again via the first subset 319 of channels, but at the increased stimulation levels.

For example, in FIG. 3D, the shaded sliders show the positions of the T-levels and C-levels from FIG. 3C. The non-shaded sliders show the positions of the T-levels and C-levels of the first subset 319 of channels after having been increased by 4 units from the positions shown in FIG. 3C. In operation, the C-levels and T-levels may be increased by 1 unit (as shown on the axis 308 on the left side of the complex user interface 301) in response to an individual indication that the sound sensation corresponding to the second set of stimulation signals generated via the first subset 319 of channels is not uncomfortably loud. However, in other embodiments, the C-levels and T-levels may be increased by more than 1 unit in response to each individual indication that the corresponding sound sensation is not uncomfortably loud. Similarly, in some embodiments, the C-levels may be increased while the T-levels may remain unchanged. Additionally, in some embodiments, the stimulation levels may be increased by a certain percentage amount (e.g., 1%) instead of a unit amount in response to each individual indication.

Figure 3E:
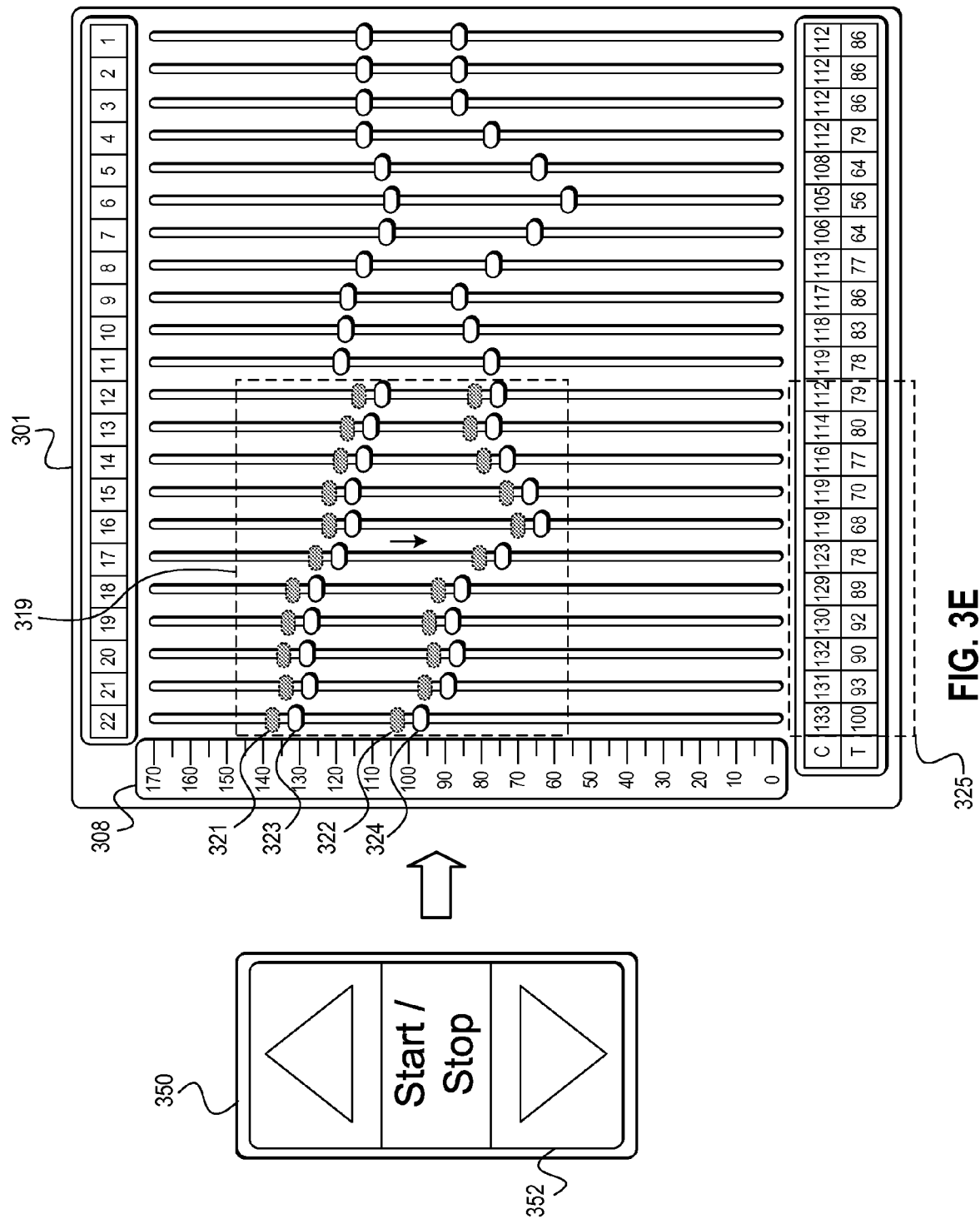
Figure 3F:
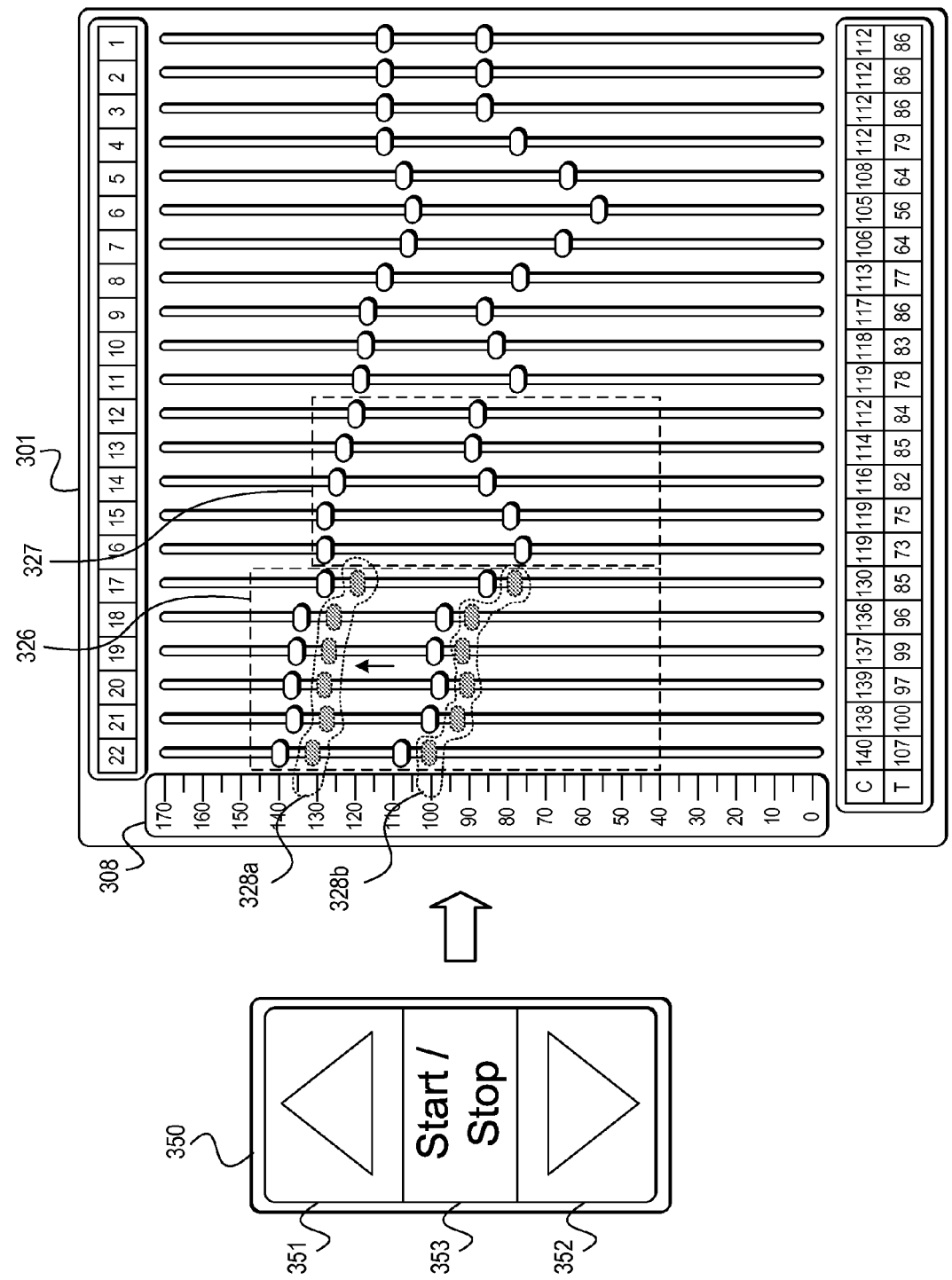

In response to receiving an indication that the sound sensation corresponding to the second set of stimulation signals generated via the first subset 319 of channels is uncomfortably loud, the hearing prosthesis (i) reduces the stimulation levels (FIG. 3E) of the second set of stimulation signals that were generated via the first subset 319 of channels and (ii) generates a third set of stimulation signals at the reduced stimulation levels via a third subset 326 of channels (FIG. 3F).

FIG. 3E shows the stimulation levels (e.g., the C-levels and T-levels) of the second set of stimulation signals generated via the first subset 319 of channels being reduced in response to receiving an indication that the sound sensation corresponding to the second set of stimulation signals is uncomfortably loud. The indication that the sound sensation corresponding to the second set of stimulation signals is uncomfortably loud is an input from the prosthesis recipient via the down input 352 of the simplified user interface 350. However, the indication may be received through other types of inputs on other types of user interfaces as well.

In FIG. 3E, the stimulation levels of the second set of stimulation signals associated with the first subset of channels 319 have been uniformly reduced by 5 units, as shown on the axis 308 on the left side of the complex user interface 301. For example, with reference to channel 22, the shaded slider 321 corresponds to the previous C-level setting for channel 22 having a value of 138 (see FIG. 3D), and the shaded slider 322 corresponds to the previous T-level setting for channel 22 having a value of 105 (see FIG. 3D). The slider 323 corresponds to the C-level setting for channel 22 having a value of 133, and the slider 324 corresponds to the T-level setting for channel 22 having a value of 100 after the stimulation levels of the second set of stimulation signals have been reduced by 5 units in response to receiving the indication that the sound sensation corresponding to the second set of stimulation signals is uncomfortably loud. Channels 12-21 in the first subset 319 of channels have similarly been reduced by 5 units, as shown in box 325 at the bottom of the complex user interface 301.

Although the example of FIG. 3E shows the stimulation levels for the stimulation signals on all 11 channels in the first subset 319 of channels having been reduced by 5 units, other embodiments may reduce the stimulation levels by more or less than 5 units. Similarly, the example of FIG. 3E shows both the C-levels and T-levels being reduced by 5 units, but some embodiments may reduce only the C-levels while leaving the T-levels unchanged. Additionally, the example of 3E shows all the stimulation levels being reduced by a uniform number of units, but in some embodiments, the stimulation levels may be reduced by percentages rather than units. For example, instead of reducing all the stimulation levels by 5 units, as measured by the index 308, all of the stimulation levels could be reduced by 5% or 1% or any other percentage amount.

The example shown in FIG. 3E illustrates the first of at least two actions that are performed in response to receiving an indication that the sound sensation corresponding to the second set of stimulation signals is uncomfortably loud. In particular, FIG. 3E shows one example of reducing the stimulation levels of the second set of stimulation signals in response to receiving an indication that a sound sensation corresponding to the second set of stimulation signals is uncomfortably loud. FIG. 3F shows the second of at least two actions that are taken in response to receiving the indication that the sound sensation corresponding to the second set of stimulation signals is uncomfortably loud. In particular, FIG. 3F shows one example of generating a third set of stimulation signals at the reduced stimulation levels via a third subset 326 of the first subset 319 of channels (FIGS. 3D-E).

FIG. 3F shows the first subset 319 of channels (FIGS. 3D-E) divided into (i) a third subset 326 of one or more channels including channels 17-22 and (ii) a fourth subset 327 of one or more channels including channels 12-16. Some embodiments include dividing the first subset 319 of channels (FIGS. 3D-E) into the third subset 326 of one or more channels and the fourth subset 327 of one or more channels in response to receiving the indication that the sound sensation corresponding to the second set of stimulation signals generated via the first subset 319 of channels (FIGS. 3D-E) is uncomfortably loud. Other embodiments include dividing the first subset 319 of channels 309 (FIGS. 3D-E) into the third subset 326 of one or more channels and the fourth subset 327 of one or more channels as part of an initialization procedure. In some embodiments, the initialization procedure divides and assigns some or all 22 channels to various sets and subsets before the first or second sets of stimulation signals are generated via the corresponding original set of channels 309 (FIGS. 3A-B) or the first subset 319 of channels (FIGS. 3D-E). In other embodiments, the initialization procedure divides the first subset 319 of channels (FIGS. 3D-E) into the third subset 326 and fourth subset 327 after the second set of stimulation signals has been generated, but before the third set of stimulation signals are generated via the third subset 326 of channels. Dividing the channels into various sets and subsets as part of an initialization procedure is described in more detail herein with respect to FIG. 4.

Regardless of when (or how) the first subset 319 of channels (FIGS. 3D-E) may have been divided into the third subset 326 of one or more channels and the fourth subset 327 of one of more channels, the aforementioned second of at least two actions that are taken in response to receiving the indication that the sound sensation corresponding to the second set of stimulation signals is uncomfortably loud is the act of generating a third set of stimulation signals at the reduced stimulation levels via the third subset 326 of channels.

In FIG. 3F, a third set of stimulation signals is generated at the reduced stimulation levels via the third subset 326 of one or more channels. For example, the reduced stimulation levels for each of the 6 channels (channels 17-22) in the third subset 326 of one or more channels are indicated by the shaded sliders 328a, 328b.

In some embodiments, the third set of stimulation signals correspond to a sound have a substantially flat frequency spectrum over a particular frequency band. In some embodiments, the particular frequency band corresponds to the range of frequencies assigned to the channels in the third subset 326 of one or more channels. For example, in FIG. 3F, if particular audio frequency ranges have been assigned to particular channels of the prosthesis, the third set of one or more stimulation signals is based on a sound having a substantially flat frequency spectrum across the frequencies corresponding to the channels in the third subset 326 of one or more channels. In some embodiments, the sound corresponds to white noise. In other embodiments, however, the sound need not be white noise nor even have a substantially flat frequency spectrum.

When the prosthesis generates the third set of stimulation signals via the third subset 326 of channels, the prosthesis recipient experiences a sound sensation corresponding to the third set of stimulation signals. In response, the prosthesis recipient may indicate whether the sound sensation corresponding to the third set of stimulation signals is (or is not) uncomfortably loud via the up input 351 or the down input 352 of the simplified user interface 350. In response to receiving an indication that the sound sensation corresponding to the third set of stimulation signals generated via the third subset 326 of channels is not uncomfortably loud, the hearing prosthesis (i) increases the stimulation levels of the third set of stimulation signals and (ii) generates the third set of stimulation signals again via the third subset 326 of channels, but at the increased stimulation levels.

For example, in FIG. 3F, the shaded sliders 328a, 328b show the positions of the T-levels and C-levels from FIG. 3E. The non-shaded sliders show the positions of the T-levels and C-levels of the third subset 326 of channels after having been increased by 7 units from the positions shown in FIG. 3E. In operation, the C-levels and T-levels may be increased by 1 unit (as shown on the axis 308 on the left side of the complex user interface 301) in response to each individual indication that the sound sensation corresponding to the third set of stimulation signals generated via the third subset 326 of channels is not uncomfortably loud. However, in other embodiments, the C-levels and T-levels may be increased by more than 1 unit in response to each individual indication that the corresponding sound sensation is not uncomfortably loud. Similarly, in some embodiments, the C-levels may be increased while the T-levels may remain unchanged. Additionally, in some embodiments, the stimulation levels may be increased by a certain percentage amount (e.g., 1%) instead of a single unit amount.

The fitting procedures illustrated in FIGS. 3A-3F can be similarly carried out for other sets and subsets of the prosthesis channels. For example, the procedures illustrated for the third subset 326 could similarly be carried out for the fourth subset 327. Likewise, the procedures illustrated for the first subset 319 could be similarly carried out for the second subset 320, and then for a fifth and sixth subset (not shown). Furthermore, the described procedures could be carried out for smaller and smaller subsets, such as, for example, seventh and eighth subsets (not shown) of the third subset 326, and ninth and tenth subsets (not shown) of the fourth subset 327.

Figure 4:
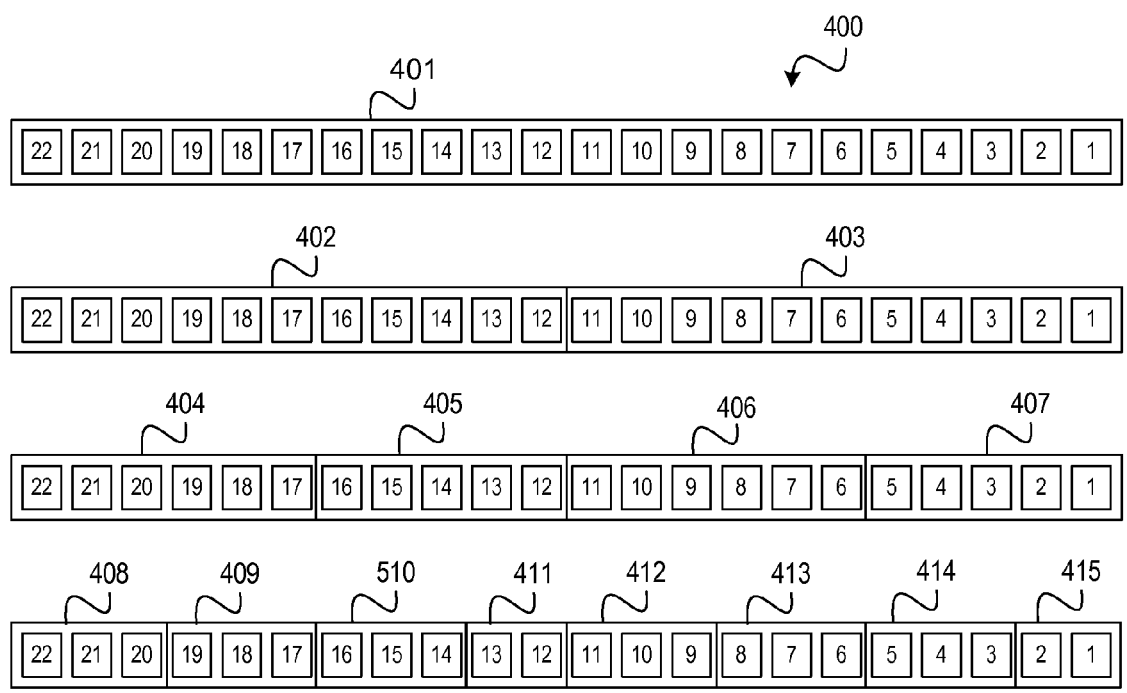

Some embodiments use channel groupings as a way to organize the sets and subsets described with respect to FIGS. 3A-F. For example, FIG. 4 shows an example 400 of different groupings of hearing prosthesis channels according to some embodiments of the disclosed systems, methods, and articles of manufacture. For a 22-channel hearing prosthesis, such as some types of cochlear implants, a first group 401 of channels includes all 22 channels, similar to the set of channels 309 shown in FIG. 3A. Likewise, a second group 402 includes channels 12-22, and a third group 403 includes channels 1-11, similar to the first subset 319 and second subset 320, respectively, as shown in FIGS. 3C-E. A fourth group 404 includes channels 17-22, a fifth group 405 includes channels 12-16, a sixth group 406 includes channels 6-11, and a seventh group 407 includes channels 1-5. Additionally, an eighth group 408 includes channels 20-22, a ninth group 409 includes channels 17-19, a tenth group 410 includes channels 14-19, an eleventh group 411 includes channels 12-13, a twelfth group 412 includes channels 9-11, a thirteenth group 413 includes channels 6-8, a fourteenth group 414 includes channels 3-5, and a fifteenth group 415 includes channels 1-2. In some embodiments, the channels may be further subdivided into smaller and smaller groups until the point where the last groups contain only a single channel.

Figure 6:
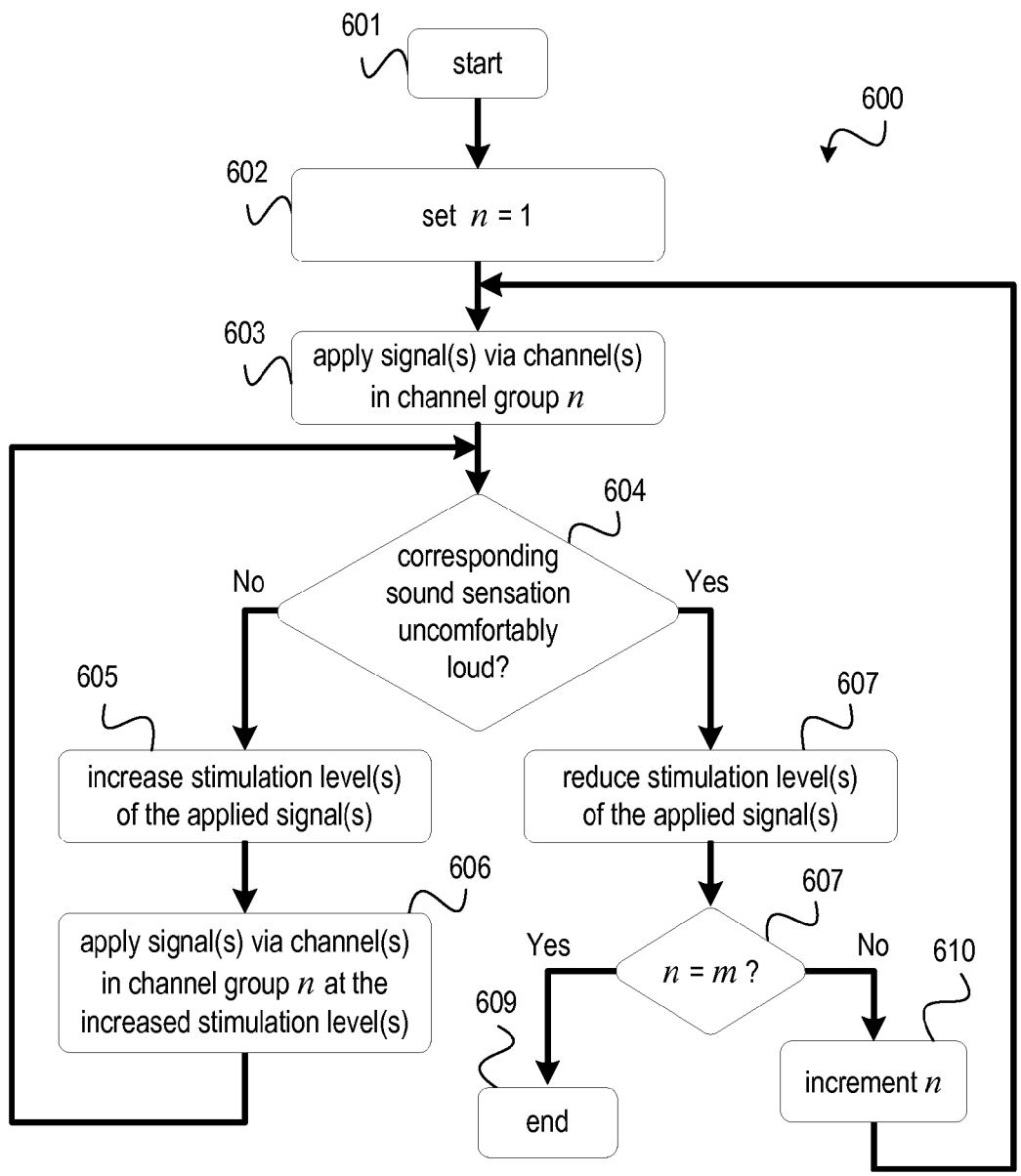
FIG. 6 shows an example algorithm for configuring a hearing prosthesis according to some embodiments of the disclosed systems, methods, and articles of manufacture.

Channel groupings similar to the ones shown and described with respect to FIG. 4 may be helpful when implementing certain algorithms for fitting a hearing prosthesis to a recipient, such as the algorithms shown and described with respect to FIG. 6 herein. Channel groupings other than the groupings shown and described with respect to FIG. 4 may be used as well.

Methods for Configuring Hearing Prostheses

Figure 5:
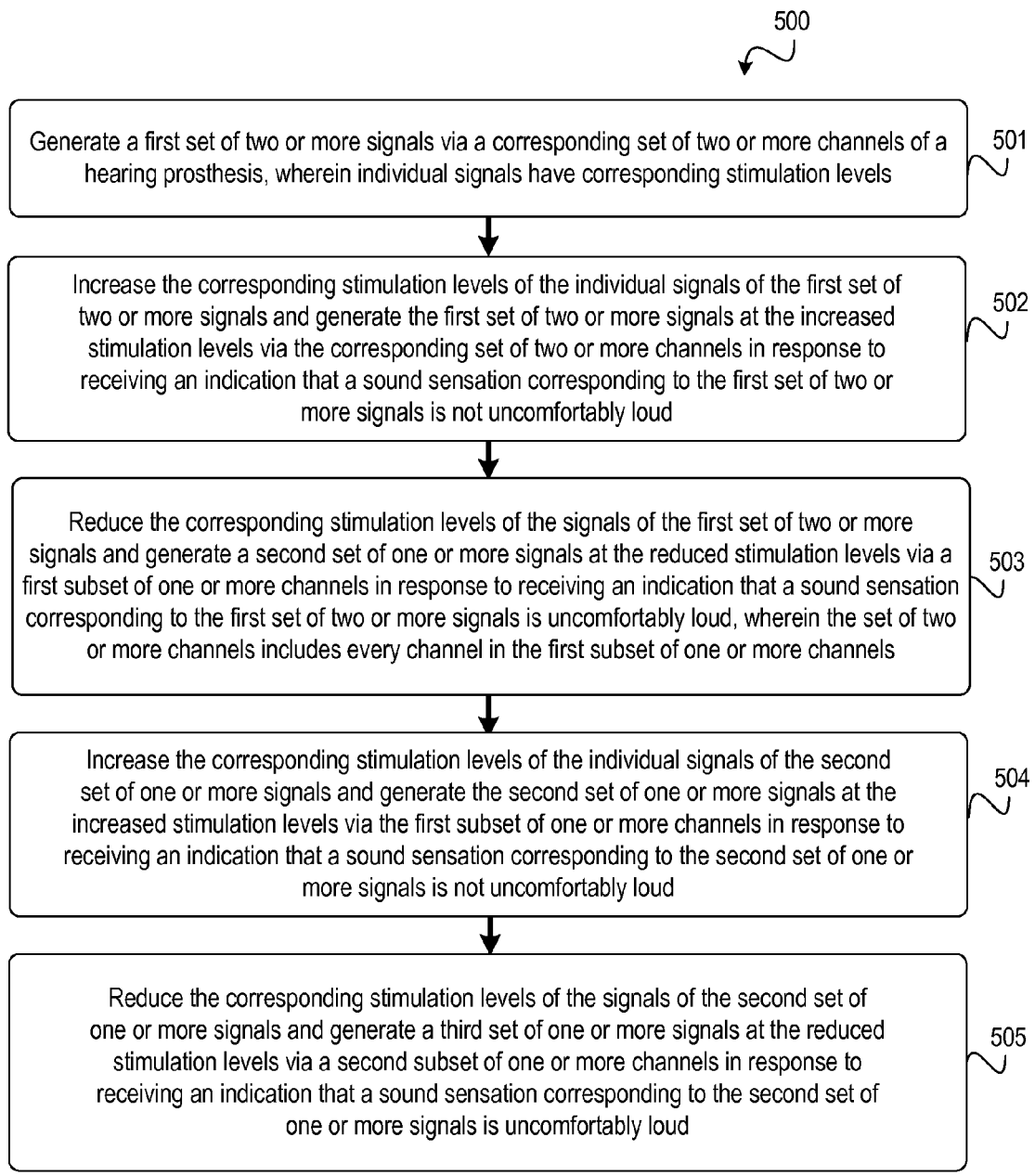
FIG. 5 shows an example method for configuring a hearing prosthesis according to some embodiments of the disclosed systems, methods, and articles of manufacture.

FIG. 5 shows an example method for configuring a hearing prosthesis according to some embodiments of the disclosed systems, methods, and articles of manufacture.

The example method 500 starts at method block 501. Method block 501 includes generating a first set of two or more signals via a corresponding set of two or more channels of a hearing prosthesis. Individual signals have corresponding stimulation levels. In some embodiments, the first set of two or more signals correspond to a sound having a substantially flat frequency spectrum (e.g., white noise) over a first frequency band. However, other sounds (with or without a substantially flat frequency spectrum) could be used as well. In some embodiments, the hearing prosthesis is a cochlear implant, and the signals of the first set of two or more signals are similar to the stimulation signals shown and described herein with respect to FIG. 2.

Method block 502 includes increasing the corresponding stimulation levels of the individual signals of the first set of two or more signals and generating the first set of two or more signals at the increased stimulation levels via the corresponding set of two or more channels in response to receiving an indication that a sound sensation corresponding to the first set of two or more signals is not uncomfortably loud. In some embodiments, increasing the stimulation levels of the individual signals and generating the first set of two or more signals at the increased stimulation levels may be similar to the procedures shown and described herein with respect to FIGS. 3A-F. Similarly, the indication that the sound sensation is not uncomfortably loud may be similar to the indications shown and described herein with respect to FIGS. 3A-F.

Method block 503 includes reducing the corresponding stimulation levels of the signals of the first set of two or more signals and generating a second set of one or more signals at the reduced stimulation levels via a first subset of one or more channels in response to receiving an indication that a sound sensation corresponding to the first set of two or more signals is uncomfortably loud. The set of two or more channels includes every channel in the first subset of one or more channels. In some embodiments, the second set of one or more signals corresponds to a sound having a substantially flat frequency spectrum (e.g., white noise) over a second frequency band. However, other sounds (with or without a substantially flat frequency spectrum) could be used as well. Similarly, in some embodiments, the signals of the second set of one or more signals are similar to the signals shown and described herein with respect to FIG. 2.

In some embodiments, reducing the stimulation levels of the first set of two or more signals and generating a second set of one or more signals are similar to the procedures shown and described herein with respect to FIGS. 3A-F. Similarly, the indication that the sound sensation is uncomfortably loud is similar to the indications shown and described herein with respect to FIGS. 3A-F.

Some embodiments additionally include method blocks 604 and 605. Method block 604 includes increasing the corresponding stimulation levels of the individual signals of the second set of one or more signals and generating the second set of one or more signals at the increased stimulation levels via the first subset of one or more channels in response to receiving an indication that a sound sensation corresponding to the second set of one or more signals is not uncomfortably loud. Method block 505 includes reducing the corresponding stimulation levels of the signals of the second set of one or more signals and generating a third set of one or more signals at the reduced stimulation levels via a second subset of one or more channels in response to receiving an indication that a sound sensation corresponding to the second set of one or more signals is uncomfortably loud. In some embodiments, the first subset of one or more channels includes every channel in the second subset of one or more channels. In other embodiments, the first subset of one more channels is mutually exclusive of the second subset of one or more channels. The functions of method blocks 504 and 505 are similar to the functions of method blocks 502 and 503, but with different sets of stimulation signals generated via different sets of channels.

In some embodiments, the second set of one or more signals corresponds to a sound having a substantially flat frequency spectrum over a second frequency band, and the third set of one or more signals corresponds to a sound having substantially flat frequency spectrum over a third frequency band. However, other sounds (with or without a substantially flat frequency spectrum) could be used as well. Similarly, in some embodiments, the signals of the second set of one or more signals and the third set of one more signals are similar to the signals shown and described herein with respect to FIG. 2.

Some embodiments of method blocks 502-505 may additionally or alternatively include decreasing and/or increasing one or more of a pulse rate, a pulse width, and/or a phase gap of at least one stimulation signal in response to receiving an indication of whether a sound sensation corresponding to the stimulation signal is uncomfortably loud. Additionally, in some embodiments, the features and functions described in method 500 may be performed by a hearing prosthesis. In other embodiments, the method 500 may be performed by a hearing prosthesis in combination with an external computing device associated with the hearing prosthesis.

Algorithms for Configuring Hearing Prostheses

FIG. 6 shows an example algorithm 600 for configuring a hearing prosthesis according to some embodiments of the disclosed systems, methods, and articles of manufacture. The configuration algorithm 600 is for use in connection with a cochlear implant, such as the cochlear implant shown and described herein with respect to FIG. 1. However, the configuration algorithm 600 is equally applicable to other types of hearing prostheses.

The configuration algorithm 600 starts at block 601. At block 602, the variable n is set to 1. In operation, the configuration algorithm 600 uses the variable n to keep track of a current channel group. The hearing prosthesis has m different channel groups, and the configuration algorithm 600 steps through each channel group from channel group 1 through channel group m. However, the configuration algorithm 600 need not step all the way through the channel groups to channel group m. In some embodiments, the configuration algorithm 600 may step through only 1, 2, 3, 4, or some other number of channel groups without going all the way to channel group m, as described herein. In some embodiments, the channels of the hearing prosthesis are pre-grouped or otherwise pre-organized similarly to the channel groups shown and described herein with respect to FIG. 4. However, in other embodiments, the channel groupings and subgroupings may are formed successively (not shown) as the configuration algorithm 600 (or a similar algorithm) is executed.

At block 603, the hearing prosthesis applies (or is instructed to apply) one or more signals via the one or more channels of channel group n. Because the n variable was set to a value of 1 at block 602, the configuration algorithm 600 initially starts with the first channel group corresponding to all the channels of the hearing prosthesis. In some embodiments, the signals of block 603 may be similar to the signals shown and described herein with respect to FIG. 2. In some embodiments, the one or more signals correspond to a sound having a substantially flat frequency spectrum (e.g., white noise) over a defined frequency band. However, other sounds (with or without a substantially flat frequency spectrum) could be used as well.

At block 604, a determination is made as to whether a sound sensation corresponding to the one or more signals applied in block 603 is or is not uncomfortably loud. The determination is based on an indication received from a prosthesis recipient. In some embodiments, the indication corresponds to an input received by the prosthesis. In other embodiments, the indication corresponds to an input received via a computing device associated with the hearing prosthesis. If the sound sensation corresponding to the one or more signals of block 603 is not uncomfortably loud, then the configuration algorithm 600 proceeds to block 705. But if the sound sensation corresponding to the one or more signals of block 603 is uncomfortably loud, then the configuration algorithm 600 proceeds to block 607.

At block 605, the stimulation levels of the one or more signals applied in block 603 are increased. And at block 606, the one or more signals are applied via the one or more channels of channel group n at the increased stimulation levels. For example, in some embodiments, increasing the stimulation levels and applying the signals at the increased stimulation levels may be similar to some of the procedures shown and described herein with respect to FIGS. 3A-F. In some embodiments, block 605 may additionally or alternatively include increasing one or more of a pulse width, a pulse rate, or a phase gap of the one of more signals. After the one or more signals have been applied at the increased levels at block 606, the configuration algorithm 600 returns to block 604, where a determination is made as to whether a sound sensation corresponding to the one or more signals applied at block 606 is uncomfortably loud.

If it is determined at block 604 that the sound sensation corresponding to the one or more signals of block 603 (or block 606) is uncomfortably loud, then the configuration algorithm 600 proceeds to block 607. At block 607, the stimulation levels of the one or more signals applied in block 603 (or block 606) are decreased. For example, in some embodiments, decreasing the stimulation levels may be similar to some of the procedures shown and described herein with respect to FIGS. 3A-F. In some embodiments, block 607 may additionally or alternatively include decreasing one or more of a pulse width, a pulse rate, or a phase gap of the one or more signals.

After block 607, the configuration algorithm 600 proceeds to block 608, where a determination is made as to whether the current value of the variable n is equal to the value of variable m, where the variable m corresponds to the total number of channel groups. If the value of the variable n is equal to the total number of channel groups, m, then the configuration algorithm 600 ends at block 609. But if the value of the variable n is not equal to the total number of channel groups, m (i.e., if the algorithm has not been applied to all the channel groups), the configuration algorithm 600 proceeds to block 610 where a determination is made as to whether to continue with the configuration algorithm 600. The determination is based on an indication received from a prosthesis recipient. In some embodiments, the indication corresponds to an input received by the prosthesis. In other embodiments, the indication corresponds to an input received via a computing device associated with the hearing prosthesis.

If the configuration algorithm 600 is not to be continued at block 610, the configuration algorithm 600 ends at block 611. But if the configuration algorithm 600 is to be continued at block 610, then the value of the variable n is incremented at block 612. After incrementing n at block 612, the configuration algorithm 600 returns to block 603 and proceeds to perform the algorithm steps with the next channel group.

Allowing the configuration algorithm 600 to continue (or not) at block 610 before the configuration algorithm 600 has stepped through all the channel groups allows the configuration algorithm 600 to be completed very quickly if desired. For example, the configuration algorithm 600 could be completed after adjusting just a few channel groups (or even adjusting just the first channel group). But if the configuration algorithm 600 is continued at block 612, then the prosthesis recipient may achieve a better fitting result because the fitting result should improve as the configuration algorithm 600 steps through additional channel groups. As a result, the configuration algorithm 600 may provide the prosthesis recipient with an incentive to continue with the configuration algorithm 600 at block 612.

Computing Devices for Configuring Hearing Prostheses

Figure 7:
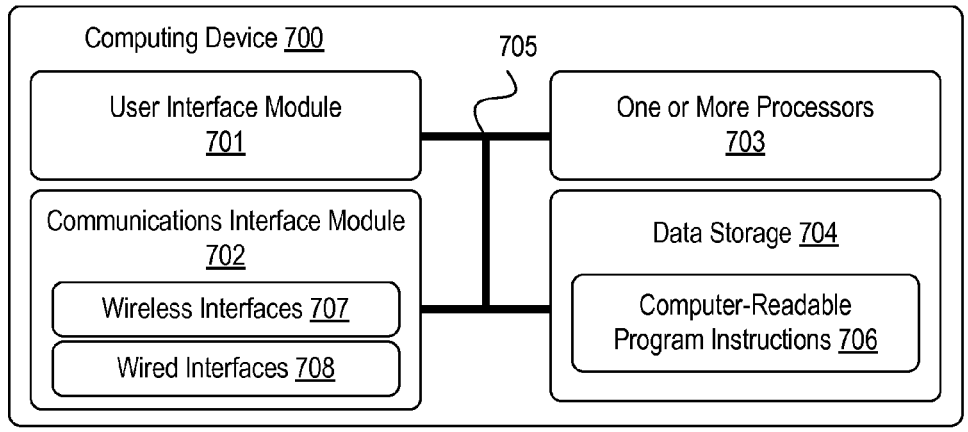
FIG. 7 shows an example of a computing device used to implement certain aspects of some embodiments of the disclosed systems, methods, and articles of manufacture.

FIG. 7 shows an example of a computing device 700 for use in implementing certain aspects of some embodiments of the disclosed systems, methods, and articles of manufacture.

The computing device 700 includes a user interface module 701, a communications interface module 702, one or more processors 703, and data storage 704, all of which are linked together via a system bus or other connection mechanism 705.

The user interface module 701 is configured to send data to and/or receive data from external user input/output devices such as a keyboard, a keypad, a touch screen, a computer mouse, a track ball, a joystick, and/or other similar devices, now known or later developed. Additionally, the user interface module 701 is also configured to provide outputs to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 701 may also be configured to generate audible output(s), such as a speaker, speaker jack, audio output port, audio output device, earphones, and/or other similar devices, now known or later developed.

In some embodiments, the user interface module 801 also includes (or is communicatively coupled to) an LCD or similar type of touch screen configured to display a user interface such as the interfaces shown and described herein with respect to FIGS. 3A-F. The touch screen may also be configured to receive indications of whether sound sensations corresponding to stimulation signals are uncomfortably loud, similar to the indications shown and described herein with respect to FIGS. 3A-F.

The communications interface module 702 includes one or more wireless interfaces 707 and/or wired interfaces 708 configured to send and receive data to/from a hearing prosthesis via a communications link. The wireless interfaces 807 may include one or more wireless transceivers, such as a Bluetooth transceiver, a Wi-Fi transceiver, a WiMAX transceiver, and/or other similar type of wireless transceiver configurable to communicate via a wireless protocol. The wired interfaces 708 may include one or more wired transceivers, such as an Ethernet transceiver, a Universal Serial Bus (USB) transceiver, or similar transceiver configurable to communicate via a twisted pair wire, a coaxial cable, a fiber-optic link or a similar physical connection.

The one or more processors 703 may include one or more general purpose processors (e.g., microprocessors manufactured by Intel, Apple, Advanced Micro Devices, etc.) and/or one or more special purpose processors (e.g., digital signal processors, application specific integrated circuits, etc.). The one or more processors 703 are configured to execute computer readable program instructions 706 contained in the data storage 704 and/or other instructions based on prosthesis fitting algorithms, such as instructions to perform certain aspects of the methods and algorithms described herein with respect to FIGS. 3-6.

The data storage 704 includes one or more computer readable storage media that can be read or accessed by at least one of the processors 703. The one or more computer-readable storage media includes volatile and/or non-volatile storage components, such as optical, magnetic, organic or other memory or disc storage, which can be integrated in whole or in part with at least one of the processors 703. In some embodiments, the data storage 704 is implemented using a single physical device (e.g., one optical, magnetic, organic or other memory or disc storage unit), while in other embodiments, the data storage 704 is implemented using two or more physical devices. The data storage 704 includes computer readable program instructions 706 and perhaps additional data. In some embodiments, the data storage 704 includes storage required to perform at least some aspects of the methods and algorithms described herein with respect to FIGS. 3-6.

Computer Readable Media Implementations

In some embodiments, the disclosed features and functions of the systems, methods, and algorithms shown and described herein are implemented as computer program instructions encoded on a computer readable media in a machine readable format.

Figure 8:
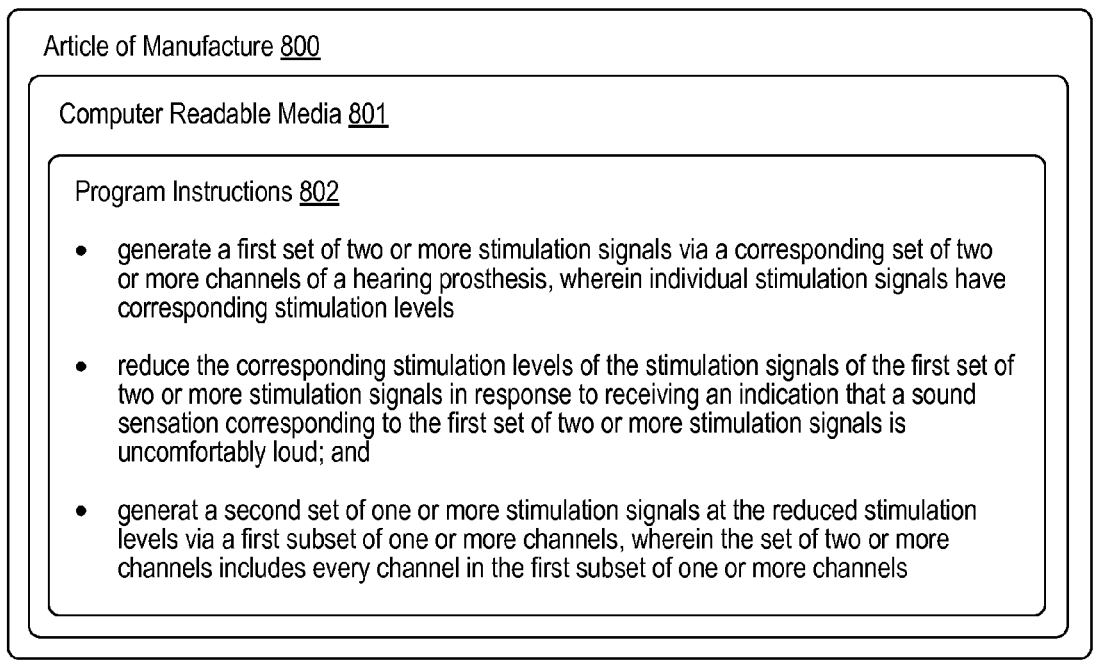
FIG. 8 shows an example of an article of manufacture including computer readable media with instructions for configuring a hearing prosthesis according to some embodiments of the disclosed systems and methods.

FIG. 8 shows an example of an article of manufacture 800 including computer readable media 801 with program instructions 802 for configuring a hearing prosthesis according to some embodiments of the disclosed systems and methods. FIG. 8 shows a schematic illustrating a conceptual partial view of an example article of manufacture 800 including computer program instructions 802 for executing a computer program. The computer-readable media 801 may be, for example, a hard disk drive, a Compact Disc (CD), a Digital Video Disk (DVD), a digital tape, or flash memory, etc. The program instructions 802 are computer executable and/or logic implemented instructions.

In embodiments where the hearing prosthesis is configured to perform the methods and algorithms described herein, the article of manufacture 800 corresponds to a hearing prosthesis 101 (FIG. 1), and the computer readable media 801 corresponds to the data storage 106 (FIG. 1). Similarly, in embodiments where an external computing device is configured to perform the methods and algorithms described herein, the article of manufacture 800 corresponds to the computing device, such as a hand-hand computing device or smartphone device, and the computer readable media 801 corresponds to memory associated with computing device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   generating a first set of three or more stimulation signals via a corresponding set of three or more channels of a hearing prosthesis, wherein individual stimulation signals have corresponding stimulation levels;
   receiving an indication that a sound sensation corresponding to the first set of three or more stimulation signals is uncomfortably loud; and
   in response to receiving the indication that the sound sensation is uncomfortably loud,
      reducing the corresponding stimulation levels of the stimulation signals of the first set of three or more stimulation signals; and
      generating a second set of two or more stimulation signals at the reduced stimulation levels via a first subset of two or more channels, wherein each channel included in the first subset of two or more channels is included in the set of three or more channels and wherein a number of channels in the first subset of two or more channels is less than a number of channels in the set of three or more channels.

2. The method of claim 1, further comprising:
   receiving an indication that the sound sensation corresponding to the first set of three or more stimulation signals is not uncomfortably loud; and
   in response to receiving the indication that sound sensation is not uncomfortably loud,
      increasing the corresponding stimulation levels of the individual stimulation signals of the first set of three or more stimulation signals; and
      generating the first set of three or more stimulation signals at the increased stimulation levels via the corresponding set of three or more channels.

3. The method of claim 1, further comprising:
   dividing the set of three or more channels into at least the first subset of two or more channels and a second subset of one or more channels.

4. The method of claim 3, wherein dividing the set of three or more channels into at least the first subset of two or more channels and the second subset of one or more channels is performed prior to generating the first set of three or more stimulation signals via the corresponding set of three or more channels.

5. The method of claim 3, wherein dividing the set of three or more channels into at least the first subset of two or more channels and the second subset of one or more channels is performed in response to receiving the indication that the sound sensation corresponding to the first set of two or more stimulation signals is uncomfortably loud.

6. The method of claim 1, further comprising:
receiving an indication that a sound sensation corresponding to the first set of three or more stimulation signals is not uncomfortably loud; and
in response to receiving the indication that sound sensation is not uncomfortably loud, increasing at least one of a corresponding pulse width, pulse rate, or phase gap of one or more individual stimulation signals of the first set of three or more stimulation signals, and wherein reducing the corresponding stimulation levels of the stimulation signals of the first set of three or more stimulation signals comprises:
reducing at least one of the corresponding pulse width, pulse rate, or phase gap of two or more individual stimulation signals of the first set of three or more stimulation signals.

7. The method of claim 1, wherein the first set of three or more stimulation signals corresponds to a sound having a substantially flat frequency spectrum over a first frequency band, and wherein the second set of two or more stimulation signals corresponds to a sound having a substantially flat frequency spectrum over a second frequency band.

8. The method of claim 1, further comprising:
reducing the corresponding stimulation levels of the stimulation signals of the second set of two or more stimulation signals in response to receiving an indication that a sound sensation corresponding to the second set of two or more stimulation signals is uncomfortably loud; and
generating a third set of one or more stimulation signals at the reduced stimulation levels via a second subset of one or more channels, wherein each channel included in the second subset of one or more channels is included in the first subset of two or more channels.

9. The method of claim 1, wherein the method steps are performed by one of (i) the hearing prosthesis or (ii) the hearing prosthesis in combination with a computing device associated with the hearing prosthesis.

10. The method of claim 1, wherein the hearing prosthesis a cochlear implant.

* * * * *